(12) United States Patent
Castor

(10) Patent No.: US 7,744,935 B2
(45) Date of Patent: Jun. 29, 2010

(54) COMPOSITIONS AND METHODS FOR INHIBITING 5-α REDUCTASE

(76) Inventor: Trevor P. Castor, 469 Mystic St., Arlington, MA (US) 02474

( * ) Notice: Subject to any disclaimer, the term of this patent is extended or adjusted under 35 U.S.C. 154(b) by 0 days.

(21) Appl. No.: 11/941,677

(22) Filed: Nov. 16, 2007

(65) Prior Publication Data
US 2008/0241284 A1 Oct. 2, 2008

Related U.S. Application Data

(62) Division of application No. 10/942,484, filed on Sep. 16, 2004, now abandoned.

(60) Provisional application No. 60/503,381, filed on Sep. 16, 2003.

(51) Int. Cl.
*A61K 36/889* (2006.01)

(52) U.S. Cl. ...................... 424/727; 424/777

(58) Field of Classification Search ........................ None
See application file for complete search history.

(56) References Cited

U.S. PATENT DOCUMENTS

| | | | |
|---|---|---|---|
| 6,039,950 A | 3/2000 | Khwaja et al. | |
| 6,277,417 B1 | 8/2001 | Anderson | |
| 6,291,241 B1 * | 9/2001 | Castor et al. | 435/410 |
| 6,319,524 B1 | 11/2001 | Gregg, Jr. | |
| 6,733,796 B2 | 5/2004 | Randhava et al. | |

FOREIGN PATENT DOCUMENTS

GB  2 343 452  *  5/2000

OTHER PUBLICATIONS

Hirata (Biol. Pharm. Bull. (2007), vol. 30, No. 12, pp. 2402-2405).*
Iehlé, et al., Human Prostatic Steroid 5a-Reductase Isoforms-A Comparative Study of Selective Inhibitors. Steroid Biochem. Molec. Biol. vol. 54, No. 5/6, pp. 273-279, 1995.

* cited by examiner

*Primary Examiner*—Susan C Hoffman
(74) *Attorney, Agent, or Firm*—Burns & Levinson, LLP; Janine M. Susan

(57) ABSTRACT

Disclosed herein are compositions for controlling androgen activity in target organs and cells through the modulation of a 5-α-reductase activity. In certain aspects, these compositions are employed to modulate androgenic activity by inhibiting the formation and availability of active androgen in target cells. As a result, the present invention is directed toward the treatment of a wide variety of conditions including, but not limited to, the treatment of prostatic hyperplasia, prostatic cancer, hirsutism, acne, male pattern baldness, seborrhea, and other diseases related to androgen hyperactivity. Several of these compositions have been shown to effectively decrease body weight, and in some cases, to decrease the weight of an androgen-dependent body organ, such as the prostate and other organs.

1 Claim, 13 Drawing Sheets

Certificate of Analysis
Saw Palmetto
5 - Alpha Reductase Assay

| ANALYST: | MJ | ASSAY DATE: | 02/07/01 | CLIENT: | Aphios |
|---|---|---|---|---|---|
| ORDER #: | 10045 | NB ID: | 1116-80 | CONTACT: | Trevor Castor |
| INVOICE #: | 110847 | | | BioFIT™ Pass Criteria | |
| Released by: | _signature_ | | | Test product statistically equal to or better than reference | |
| Date: | 2/12/01 | | | | |

| ASSAY CODE | SAMPLE ID | % Inhibition | Average % Inhibition | SD | BioFIT™ Evaluation |
|---|---|---|---|---|---|
| A | REFERENCE | 56<br>55<br>53 | 55 | 2 | IN COMPLIANCE |
| B | Aphios<br>SP-15-A<br>Locker 05-074 | 54<br>54<br>55 | 54 | 1 | PASS |
| C | Aphios<br>SP-15-B<br>Locker 05-075 | 49<br>51<br>52 | 51 | 2 | PASS |
| D | Aphios<br>SP-15-C<br>Locker 05-076 | 9<br>8<br>8 | 8 | 1 | FAIL |
| E | Aphios<br>SP-16-A<br>Locker 05-077 | 34<br>34<br>32 | 33 | 1 | FAIL |
| F | Aphios<br>SP-16-B<br>Locker 05-078 | 4<br>3<br>2 | 3 | 1 | FAIL |
| G | Aphios<br>SP-16-C<br>Locker 05-079 | 7<br>-1<br>2 | 3 | 4 | FAIL |

FIG. 4

Certificate of Analysis
Saw Palmetto
5 - Alpha Reductase Assay

| ANALYST: | MJ | ASSAY DATE: | 02/09/01 | CLIENT: | Aphios |
|---|---|---|---|---|---|
| ORDER #: | 10045 | NB ID: | 1116-85 | CONTACT: | Trevor Castor |
| INVOICE #: | | 110847 | | BioFIT™ Pass Criteria | |
| Released by: | | *[signature]* | | Test product statistically equal to or better than reference | |
| Date: | | 2/12/01 | | | |

| ASSAY CODE | SAMPLE ID | % Inhibition | Average % Inhibition | SD | BioFIT™ Evaluation |
|---|---|---|---|---|---|
| A | REFERENCE | 53<br>55 | 54 | 1 | IN COMPLIANCE |
| B | Aphios<br>SP-17-A<br>Locker 05-080 | 55<br>55<br>55 | 55 | 0 | PASS |
| C | Aphios<br>SP-17-B<br>Locker 05-081 | 53<br>58<br>54 | 55 | 3 | PASS |
| D | Aphios<br>SP-17-C<br>Locker 05-082 | 34<br>37<br>37 | 36 | 2 | FAIL |

FIG. 5

Certificate of Analysis
Saw Palmetto
5 - Alpha Reductase Assay

| ANALYST: | B. Hughes | ASSAY DATE: | 03/20/01 | CLIENT: | Aphios |
|---|---|---|---|---|---|
| ORDER #: | 10045 | NB ID: | 1101-184 | CONTACT: | Trevor Castor |
| INVOICE #: | | 110856 | | BioFIT™ Pass Criteria | |
| Released by: | | | | Test product statistically equal to or better than reference | |
| Date: 03/20/01 | | | | | |

| ASSAY CODE | SAMPLE ID | % Inhibition | Average % Inhibition | SD | BioFIT™ Evaluation |
|---|---|---|---|---|---|
| A | REFERENCE | 57<br>60<br>58 | 58 | 2 | IN COMPLIANCE |
| B | Aphios SSP-19-1 05-084 | 63<br>63<br>60 | 62 | 2 | PASS |
| C | Aphios SSP-19-1-CF 05-085 | 4<br>3 | 4 | 1 | FAIL |
| D | Aphios SSP-20-1 05-086 | 54<br>53<br>54 | 54 | 1 | PASS |
| E | Aphios SSP-20-CF 05-087 | 54<br>48<br>47 | 50 | 4 | PASS |

FIG. 6

CERTIFICATE OF ANALYSIS
SAW PALMETTO
5 - ALPHA REDUCTASE ASSAY

| ANALYST: | MJ | ASSAY DATE: | 02/18/01 | CLIENT : | APHLOS |
|---|---|---|---|---|---|
| ORDER #: | 1006 | NB ID: | 1116-92 | CONTACT: | TREVOR CASTOR |
| INVOICE #: | | 110850 | | BioFTT™ PASS CRITERIA | |
| RELEASED BY: | | | | TEST PRODUCT STATISTICALLY EQUAL TO OR BETTER THAN REFERENCE | |
| DATE: | | | | | |

| ASSAY CODE | SAMPLE ID | % INHIBITION | AVERAGE % INHIBITION | SD | BioFTT™ EVALUATION |
|---|---|---|---|---|---|
| A | REFERENCE (50 ug) | 47<br>51<br>40 | 49 | 2 | IN COMPLIANCE |
| B | REFERENCE (75 ug) | 57<br>55<br>59 | 57 | 2 | PASS |
| C | REFERENCE (25 ug) | 22<br>19<br>21 | 21 | 2 | FAIL |
| D | APHLOS (05-074) SP-15A (75 UG) | 58<br>60<br>59 | 59 | 1 | PASS |
| E | APHLOS (05-074) SP-15-A (50 ug) | 50<br>48<br>51 | 50 | 2 | PASS |
| F | APHLOS (05-074) SP-15-A (25 ug) | 23<br>20<br>21 | 21 | 2 | FAIL |

FIG. 11

COMPOSITIONS AND METHODS FOR INHIBITING 5-α REDUCTASE

CROSS-REFERENCE TO RELATED APPLICATIONS

This application is a divisional of U.S. application Ser. No. 10/942,484 filed Sep. 16, 2004, now abandoned, which claims priority to and the benefit of U.S. Provisional 60/503,381, filed Sep. 16, 2003.

FIELD OF THE INVENTION

The present invention pertains to compositions and methods for treating disease. In particular, the instant invention pertains to regulating 5-α reductase and thereby affect the physiological process leading to certain diseases.

BACKGROUND OF THE INVENTION

There are two commonly associated male physiological events that have a similar etiology. Benign prostatic hyperplasia (BPH) and male pattern baldness are both related to the enzyme 5-α reductase. (Hirsutism in women is also related to this enzyme.) An excess in activity of 5-α reductase has been shown to be responsible for BPH and male pattern baldness, as well as hirsutism in women. 5-α Reductase catalyzes the conversion of testosterone to 5α dihydrotestosterone (5α DHT). 5α DHT is a physiological ligand for an intracellular androgen receptor. The intracellular receptor has a higher affinity for 5α DHT than testosterone. Once the ligand has interacted with its cognate receptor, the receptor-ligand complex enters the nucleus and regulates gene expression.

Benign prostatic hyperplasia is the most common non-neoplastic disease process in men directly associated with aging. Although BPH has traditionally been a term used to refer to non-malignant enlargement of the prostate gland resulting from hyperplasia of the prostate epithelium and subsequent urinary outflow obstruction, recent studies have suggested that prostatic enlargement and histologic hyperplasia are only one facet of a larger syndrome consisting of both irratative and obstructive lower urinary tract symptoms, diminished urinary flow rate, and bladder dysfunction. Histologic evidence of BPH has been demonstrated in men as young as forty years; however, microscopic nodular hyperplasia associated with irritative symptoms or outlet obstruction is more commonly seen in men aged fifty to seventy. The frequency of symptomatic BPH is variable yet increases between the fifth and eighth decade of life.

Androgenetic alopecia can occur in both males and females. In men, hair loss generally occurs in the frontal, vertex, and upper occipital regions of the scalp while sparing the posterior and lateral margins. The process may begin at any age after puberty, with temporal hair recession usually noted first. There is no actual loss of hair, but rather a conversion of thick thermal hairs to fine, unpigmented hairs. In women, the pattern of hair loss is generally more diffuse with thinning throughout the scalp. Women with elevated androgen levels, as occur in masculinizing disorders, have a balding pattern similar to that of men. Treatment generally focuses on blocking the 5-α-reductase, the enzyme responsible for converting testosterone to dihydrotestosterone.

Hirsutism is the presence of excess hair in women. This phenomenon is usually an androgen-dependent process. Twenty-five to 35% of young women have terminal hair over the lower abdomen, around the nipples, or over the upper lip. Most women gradually develop more androgen-dependent body hair with age. Nevertheless, normal patterns of female hair growth are unacceptable to many women. At the other extreme, severe hirsutism may rarely be the earliest signs of masculinizing diseases. More often, however, severe hirsutism reflects only increased androgen production in women with a non serious underlying disorder.

There are other diseases associated with 5-α-reductase activity such as acne and seborrhea. The key for treating all of these diseases is the modulation of 5-α-reductase activity.

Currently there is a need for an economically feasible treatment regime that is safe and relatively inexpensive to combat diseases associated with 5-α-reductase.

SUMMARY

The present invention pertains to the utilization of certain compositions for the control of androgen activity in target organs and cells through the modulation of a 5-α-reductase activity. In certain aspects, these compositions are employed to modulate androgenic activity by inhibiting the formation and availability of active androgen in target cells. As a result, the present invention is directed toward the treatment of a wide variety of conditions including, but not limited to, the treatment of prostatic hyperplasia, prostatic cancer, hirsutism, acne, male pattern baldness, seborrhea, and other diseases related to androgen hyperactivity. Several of these compositions have been shown to effectively decrease body weight, and in some cases, to decrease the weight of an androgen-dependent body organ, such as the prostate and other organs. The effectiveness of these compositions may be dependent also on their action on other mechanisms involved in angiogenesis, cell-cell interaction, and on their interaction with various components of organs and cells.

In one embodiment, compositions useful for modulating 5-α-reductase activity are isolated from *Serenoa repens*. In a particular aspect of the present invention, the 5-α-reductase activity is inhibited by compositions of the instant invention thereby limiting the catalytic conversion of testosterone to 5α DHT. Limiting the availability of 5α DHT to target tissue is important in the treatment of diseases such as, but not limited to, benign prostatic hyperplasia, male pattern baldness, and hirsutism. In one aspect, Saw Palmetto as well as its analogs/derivatives can serve as the modulator of 5-α-reductase activity. In another aspect, Sperol as well as its analogs/derivatives can serve as the modulator of 5-α-reductase activity.

In another embodiment, methods are described which effectuate the administration of compositions of the present invention to individuals in need thereof. Individuals afflicted with a 5-α-reductase-based disease, such as prostatic hyperplasia and alike can be administered an effective amount of one or more of the compositions of the present invention.

BRIEF DESCRIPTION OF THE DRAWINGS

FIG. 4 is a certificate of analysis for 5-α-reductase inhibition using Saw Palmetto fractions;

FIG. 5 is a certificate of analysis for 5-α-reductase inhibition using Saw Palmetto fractions;

FIG. 6 is a certificate of analysis for 5-α-reductase inhibition using Saw Palmetto fractions;

FIG. 11 is a certificate of analysis for 5-α-reductase inhibition using Saw Palmetto fractions;

DETAILED DESCRIPTION

The present invention pertains to the utilization of certain compositions for the control of androgen activity in target organs and cells through the modulation of a 5-α-reductase activity. In certain aspects, these compositions are employed to modulate androgenic activity by inhibiting the formation and availability of active androgen in target cells. As a result, the present invention is directed toward the treatment of a wide variety of conditions including, but not limited to, the treatment of prostatic hyperplasia, prostatic cancer, hirsutism, acne, male pattern baldness, seborrhea, and other diseases related to androgen hyperactivity. Several of these compositions have been shown to effectively decrease body weight, and in some cases, to decrease the weight of an androgen-dependent body organ, such as the prostate. The effectiveness of these compositions may be dependent also on their action on other mechanisms involved in angiogenesis, cell-cell interaction, and on their interaction with various components of organs and cells.

Compositions useful in the practice of the present invention include Saw Palmetto, Sperol along with their respective analogs and derivatives. Saw Palmetto and Sperol originate from the same source, that is, the *Serenoa repens* berry.

An analog of the present invention is a chemically related structure that possesses similar function as that observed in the parent composition. A derivative herein refers to a composition that is a chemical derivative of a parent composition and possesses similar function as can be observed in the parent composition. Both analogs and derivatives can be modified compositions, that is, the parent composition can be modified by the addition of groups or the elimination of groups. However, it is important that the analog or derivative retain similar function to that of the parent. For example, the compositions of the present invention modulate 5-α-reductase, therefore, any derivative or analog of a parent compound must have the ability to modulate the reductase activity. Modulation can mean stimulation or inhibition. In a particular aspect of the present invention, modulation of the reductase activity refers to its inhibition.

Figure 1:
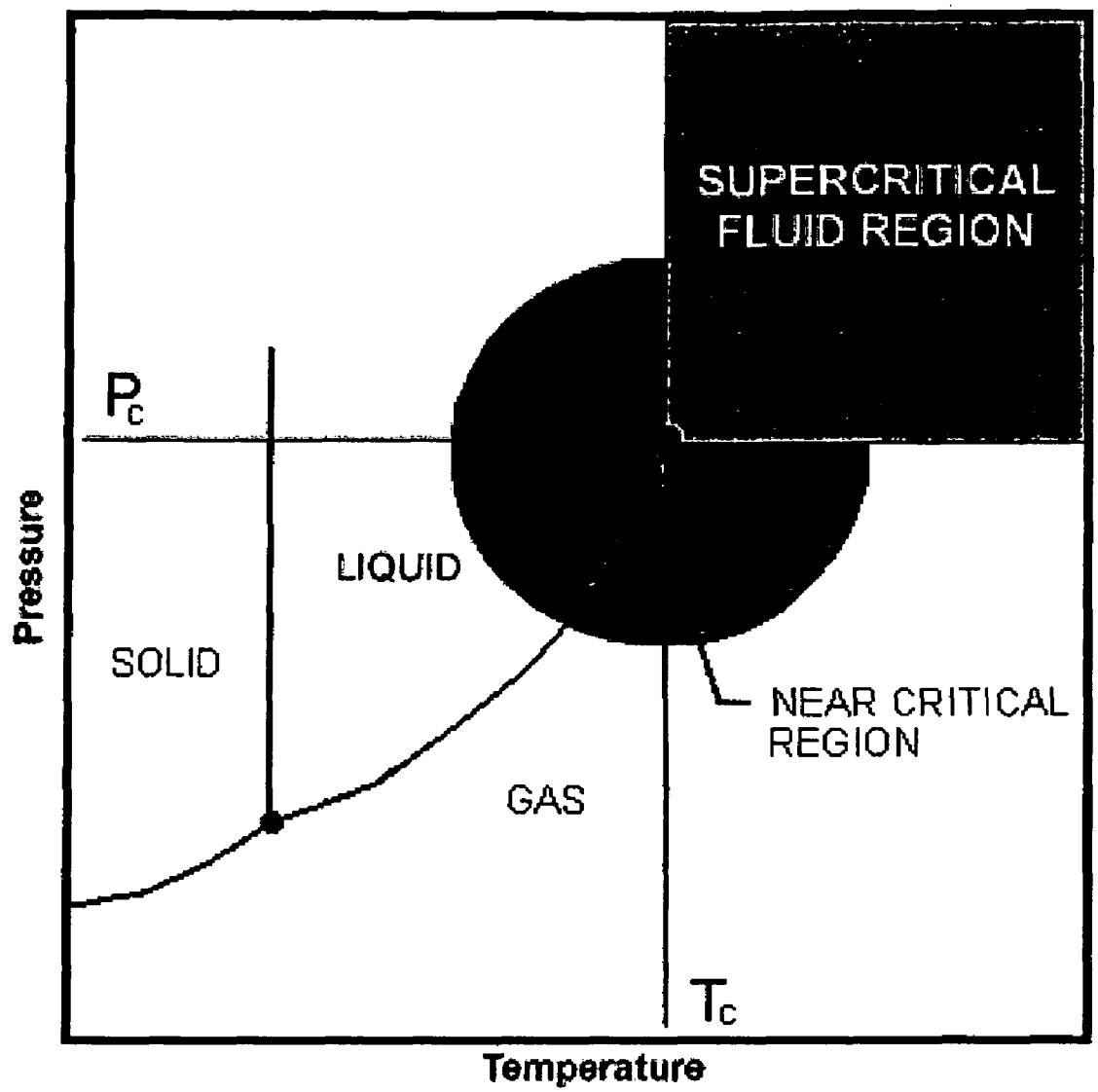
FIG. 1 is a graph illustrating the parameters for a super critical fluid.

The therapeutic compositions of the present invention have been standardized and enhanced using super-critical or near-critical fluids such as carbon dioxide with the addition of small quantities of a polar cosolvent such as an alcohol. As shown in FIG. 1, a material becomes a supercritical fluid (SCF) at conditions which equal or exceed both its critical temperature and critical pressure. These parameters are intrinsic thermodynamic properties of all sufficiently stable pure compounds and mixtures. Carbon dioxide, for example, becomes a supercritical fluid at conditions which equal or exceed its critical temperature of 31.1° C. and its critical pressure of 72.8 atm (1,070 psig). In the supercritical fluid region, normally gaseous substances such as carbon dioxide become dense phase fluids which have been observed to exhibit greatly enhanced solvating power.

At a pressure of around 3,000 psig (204 atm) and a temperature of around 40° C., carbon dioxide has a density of approximately 0.8 g/cc and behaves much like a non-polar organic solvent having a dipole moment of zero debyes. A supercritical fluid uniquely displays a wide spectrum of solvation power as its density is strongly dependent upon temperature and pressure. Temperature changes of tens of degrees or pressure changes by tens of atmospheres can change a compound's solubility in a supercritical fluid by an order of magnitude or more. This unique feature allows for the fine-tuning of solvation power and the fractionation of mixed solutes. The selectivity of non-polar supercritical fluid solvents can also be enhanced by addition of compounds known as modifiers (also referred to as entrainers or cosolvents). These modifiers are typically somewhat polar organic solvents such as acetone, ethanol and methanol. Varying the proportion of modifier allows a wide latitude in the variation of solvent power.

In addition to their unique solubilization characteristics, supercritical fluids possess other physicochemical properties that add to their attractiveness as solvents. They can exhibit liquid-like density yet still retain gas-like properties of high diffusivity and low viscosity. The latter increases mass transfer rates, significantly reducing processing times. Additionally, the ultra-low surface tension of supercritical fluids allows facile penetration into microporous materials, increasing extraction efficiency and overall yields. While similar in many ways to conventional non-polar solvents such as hexane, it is well known that supercritical fluid solvents can extract a different spectrum of materials than conventional techniques. Product volatilization and oxidation as well as processing time and organic solvent usage can be significantly reduced with the use of supercritical fluid solvents.

Figure 2:
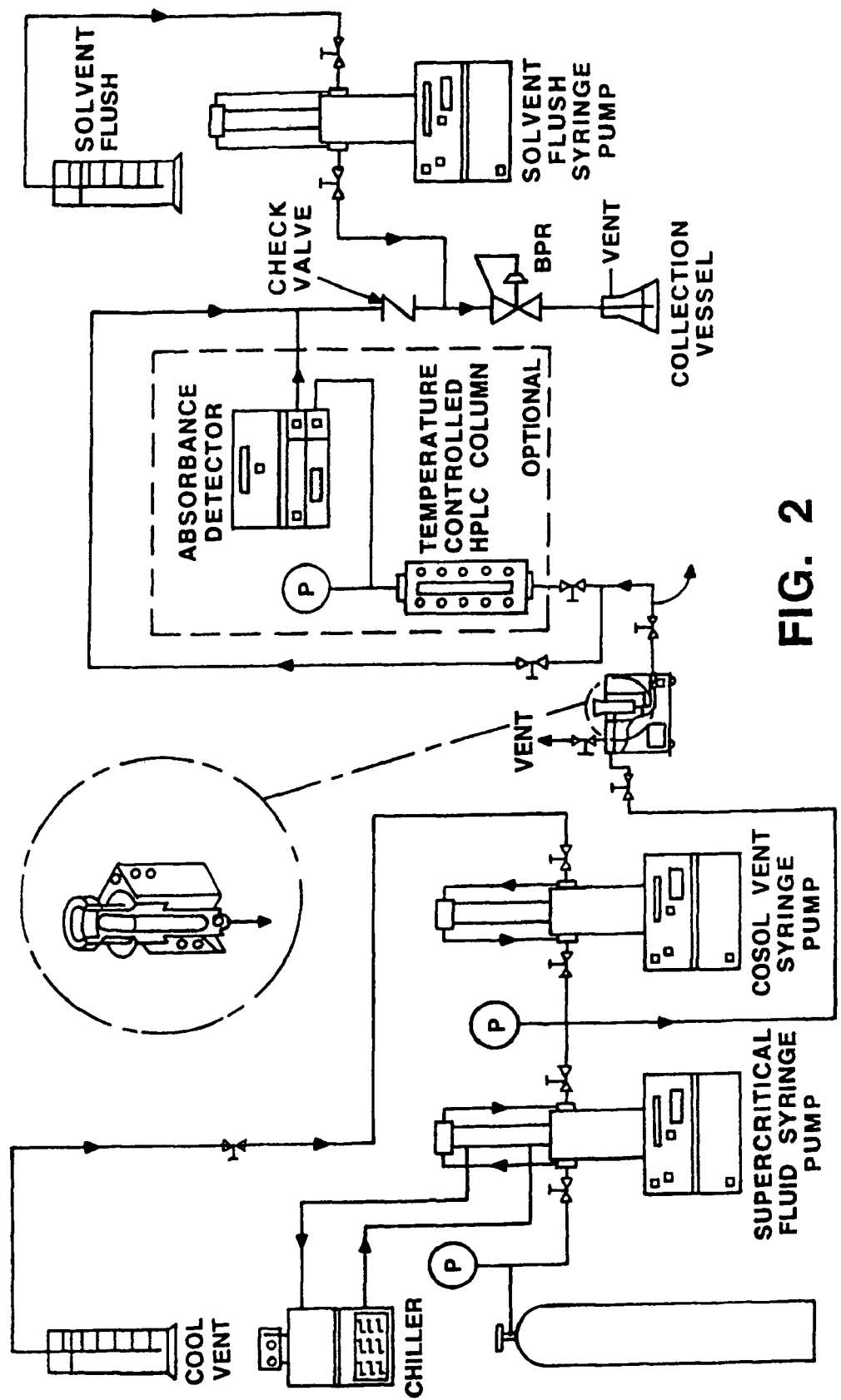
FIG. 2 is a diagram of an extraction apparatus.

To prepare an extract from Saw Palmetto (*Serenoa repens*) berries, supercritical fluid fractionation can be performed on an apparatus such as is shown in FIG. 2. This apparatus comprises a dual pump system, utilizing one syringe pump for neat supercritical near-critical or critical fluid and a second syringe pump for an alcohol co-solvent or modifier. The pumps are independently controllable, allowing easy adjustment of fluid composition.

The biomass of, for example, Saw Palmetto is ground into a fine powder (around 100 mesh). Approximately three grams of the dried powder is transferred to an extraction cartridge (e.g., ~1-100 mL), after which the cartridge is filled with glass wool or beads to reduce the dead volume. After loading a cartridge on its holder, the sequential extraction/fractionation procedure is commenced. The system is then brought to 3,000 psig and 40° C., and extracted for 30 minutes with pure carbon dioxide ($CO_2$). This fraction is collected in either ethanol or methanol in the glass collection vessel shown in FIG. 2. Next, the extraction parameters are typically set to: supercritical $CO_2$ at about 3,000 psig and extraction temperature of about 40° C., step extractions with methanol or ethanol as a co-solvent at 5, 10, 20, 30 and 40 vol %, each step being 30 min are performed. For supercritical fluid extraction and chromatographic purification (CXP), an inline HPLC column is introduced between the extractor and the backpressure regulator (FIG. 2) during the extraction step.

The present invention pertains to methods of modulating 5 α-reductase, which include subjecting a cell to an effective concentration of a 5 α-reductase modulator such as one of the compositions disclosed herein. It is believed that the use of such a modulator, for example an inhibitor, can be used to block abnormal androgen action thereby serving to treat, for example, cancer in conjunction with other anti-cancer agents, chemotherapy, resection, radiation therapy, and the like. The compositions of the present invention, besides acting as 5 α-reductase modulators, can have other effects that can lead to antitumor activity or to suppress abnormal growth of prostate or other organs.

In mammalian cells, 5 α-reductase is very tightly associated with intracellular membranes, including the membrane of the endoplasmic reticulum and contiguous nuclear membranes. An assay of 5 α-reductase activity can be performed by measuring the rate of conversion of testosterone to 5 α-DHT by whole cells or by microsomal and nuclear preparations in the presence of NADPH (enzymatic assay). Alternatively, the 5 α-reductase activity can be reliably assayed by following NADPH-dependent noncovalent binding of a potent radioactive inhibitor, such as [$^3$H]4-MA ([$^3$H]4-MA-binding assay), which strongly competes with testosterone for binding to the 5 α-reductase. The results of the two assays correlate very well when microsomal preparations from different organs or animals are used for comparison.

Briefly, the binding assay solution, in a final volume of about 0.15 mL, contains microsomes (2-20 µg of protein), about 0.07 µCi of [$^3$H]4-MA, about 0.1 mM-NADPH, about 1 mM dithiothreitol (DTT) in 50 mM-potassium phosphate buffer, pH 7.0, with or without a predetermined amount of a lipid or an inhibitor preparation. Lipids are dissolved in ethanol and added in about 1-5 µL volumes. Control tubes receive the same amount of ethanol. After incubation at around 0° C. for approximately 1 hour, the [$^3$H]4-MA bound to microsomes is determined by collecting microsomes on a Whatman glass fibre filter and washing with about 10 mL of 20 mM potassium phosphate buffer, pH 7.0, containing about 0.01% CHAPS to remove unbound [$^3$H]4-MA.

The standard reaction mixture, in a final volume of about 0.15 mL, contains micrsomes, about 1 µCi of [$^3$H]testosterone, about 0.5-3.0 µM non-radioactive testosterone, about 0.1 mM NADPH, about 1 mM DTT in a 50 mM-potassium phosphate buffer, pH 7.0, with or without the indicated amount of a lipid or an inhibitor preparation. The reaction is started by the addition of microsomes and the incubation is carried out at approximately 37° C. for about 15 minutes. Steroids are extracted and separated by thin layer chromatography (TLC). Radioactive steroids are located by fluorography and the amount of radioactivity present determined by scintillation counting. The 5 α-reductase activity can be measured by analyzing the extent of the conversion of [$^3$H]testosterone to [$^3$H]5 α-DHT.

Microsomes can be prepared at around 4° C. from a buffered 0.32 M-sucrose homogenate of human liver and from the livers of adult Sprague-Dawley female rats by differential centrifugation, and can be used in the assay of 5 α-reductase activity. In some experiments, microsomes are solubilized with approximately 0.1% polyoxyethylene ether W-1, except for the substitution of polyoxyethylene ether W-1 for Lubrolx-WX.

Cells genetically engineered to express specific types of 5 α-reductase isozymes can also be used as sources of 5 α-reductase activity. Intact cells containing 5 α-reductase, their microsomes, or nuclear preparations can also be used to screen 5 α-reductase inhibitors.

A composition of the instant invention can be used to treat various diseases such as prostatic hyperplasia. The effectiveness of such compositions can be determined either on isolated cell lines derived from diseased tissue or in animals demonstrating the particular disease. By way of example, human prostate cancer PC-3 cells are grown in culture medium. About one million cells can be injected into male nude mice and the growth of tumors followed. Within two weeks, the tumor grows to about 100 mm$^3$. Three tumor bearing mice can be injected with a test compound each day.

The present invention is also directed toward an inhibitor of 5 α-reductase that can be active topically and inactive systemically; such an agent would be ideal for treatment of androgen-dependent dermatological disorders. Especially useful in the evaluation of the effects of these topically applied compositions on skin cells or sebaceous glands is the hamster flank organ (Frost and Gomez, Adv. Biol. Skin., 1972, pp. 403-420, the entire teaching of which is incorporated herein by reference). The paired flank organs, one on each side of the costovertebral angle, are highly sensitive to androgen stimulation. The androgen sensitive structures in the flank organ include dermal melanocytes, sebaceous glands, and hair follicles. This animal model has been widely used for testing androgenic and antiandrogenic compounds. The unique advantage of this animal model is that a testing compound can be applied topically to only one of the flank organs and the effect observed on both organs. If the test compound has only a local effect, then only the treated flank organ is affected. However, if the effect is systemic, then both flank organs are affected.

Topical effects of compositions on hair loss and growth can be assessed. The stumptail macaque monkey develops baldness in a pattern resembling human androgenetic alopecia. The balding process begins shortly after puberty (approximately 4 years of age). This occurs in nearly 100% of the animals, males and females, and is androgen dependent. This is a useful animal model for human androgenetic alopecia and is contemplated to be useful in demonstrating the effects of Saw Palmetto and Sperol (as well as their analogs and derivatives) on hair loss. The following describes a protocol for testing.

Male stumptail macaques (4 years of age) can be divided into various groups of animals. A defined area of the scalp involving the frontal and vertex areas can be marked, e.g., by tattoo. Hairs in the marked area can be shaved. The solutions of a test composition in different dosages and combinations can be evenly applied to the shaved areas once or twice a day. Control animals can receive the same volume of the solvent (e.g., ethanol or other organic solvent, or a cream). The same area of the scalp can be shaved every 4 to 6 weeks and the weights of hairs shaved can then be determined. The treatments may last for 6 months to 2 years. 4-MA (17-N,N-diethylcarbamoyl-4-methyl-4-aza-5-androstan-3-one), a 5 α-reductase inhibitor known to prevent baldness in this animal can be included as a positive control. Biopsies of the scalp (4 mm punch) can be obtained before and at the end of the treatments. The specimens can be analyzed for 5 α-reductase activity and examined histologically for evidence of alopecia.

Topical antiandrogenic activity of compositions of the present invention can first be evaluated in the hamster flank organ assay. To further confirm the effectiveness of antiandrogenic compounds and suitability for human use, tests can be performed on a human male subject. The ideal compositions for human treatment are those that are topically and locally active but do not show systemic antiandrogenic activity, especially in the cases involving young males.

One or more male volunteers can be used to test and analyze sebum production from the forehead region. The forehead can be washed thoroughly with soap twice and then cleaned with 70% isopropyl alcohol twice. Sebum production can be measured 30 to 60 minutes later with a sebum meter tape probe (7 mm×8 mm) covering 56 mm$^2$ area in each measuremerit. Ten measurements can be made within the 4 cm square area (16 cm$^2$) located at the middle of the left or right side forehead between the eyebrow and the hair line.

The sebum meter detects the difference in the transparency of the tape before and after the tape was placed on the forehead for 30 seconds and expresses the difference in an arbitrary number (S-value) between 0 to 300 (or higher). S-values of sebum accumulated on the foreheads of men are usually 200 to 300. Skin surface on hands usually shows a very low number (5 to 20). The S-value for forehead immediately after washing is less than 5. For men, the S-value gradually increases to about 50 within 30 minutes after washing and reaches 100 to 200 in 45 minutes to 55 minutes.

To determine the rate of sebum production, the left and the right forehead areas can be measured alternatively and each time at the comparable areas on the two sides. Ten measurements on each side (i.e., 20 measurements for two sides) take about 15-20 minutes and the sebum-values likely range between 30 to 200. The S-values can differ considerably at different areas of the forehead and could be influenced by environmental, including weather, diet, and physiological, conditions. However, the ratio of the total S-value (the sum of 10 measurements) for the left and the total S-value for the right forehead is constant. Therefore, compounds applied to the left forehead that reduce the L/R ratio to lower than 1.1 are considered as topically active agents for suppression of sebum production.

In another embodiment, the present invention pertains to methods for administering the compositions of the instant invention to individuals in need thereof. Individuals afflicted with a 5-α-reductase-based disease, such as prostatic hyperplasia can be administered an effective amount of one or more of the compositions of the present invention in order to treat the disease.

Aqueous compositions of the present invention comprise an effective amount of one or more compositions of the present invention dissolved or dispersed in a pharmaceutically acceptable aqueous medium. The phrase "pharmaceutically acceptable" refers to molecular entities and compositions that do not produce an allergic or similar untoward reaction when administered to a subject.

The preparation of an aqueous composition that contains such an inhibitory compound as an active ingredient is well understood in the art. Typically, such compositions are prepared as injectable, either as liquid solutions or suspensions; solid forms suitable for solution in, or suspension in, liquid prior to injection can also be prepared. The preparation can also be emulsified.

The pharmaceutical compositions disclosed herein can be orally administered, for example, with an inert diluent or with an assimilable edible carrier, or they can be enclosed in hard or soft shell gelatin capsule, or can be compressed into tablets, or they can be formulated for controlled release, such as a transdermic and osmotic pressure device, injectable device, and implantable device, or they can be incorporated directly with the food of the diet. For oral therapeutic administration, the active compounds can be incorporated with excipients and used in the form of ingestible tablets, buccal tablets, troches, capsules, elixirs, suspensions, syrups, wafers, and the like. The percentage of the compositions and preparations can, of course, be varied and can conveniently be 100% (application of pure compounds). The amount of active compounds in such therapeutically useful compositions is such that a suitable dosage will be obtained. The tablets, troches, pills, capsules and the like can also contain the following: a binder, such as gum tragacanth, acacia, corn starch or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin; or a flavoring agent, such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules may be coated with shellac, sugar or both. A syrup of elixir can contain the active compounds; sucrose, as a sweetening agent, methyl and propylparabens as preservatives; a dye and flavoring, such as cherry or orange flavor. Of course, any material used in preparing any dosage unit form should be pharmaceutically pure and substantially non-toxic. In addition, the active compounds can be incorporated into sustained-release preparations and formulations.

The active compounds can also be administered parenterally, intravenously, or intraperitoneally. Solutions of the active compounds as a free base or pharmacologically acceptable salts can be prepared in water suitably mixed with a surfactant, such as hydroxypropylcellulose. Dispersions can also be prepared in glycerol, liquified polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bactcria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such a lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the composition may be incorporated with excipients and used in the form of non-ingestible mouthwashes and dentifrices. A mouthwash can be prepared incorporating the active ingredient in the required amount in an appropriate solvent, such as a sodium borate solution (Dobell's Solution). Alternatively, the active ingredient can be incorporated into an antiseptic wash containing sodium borate, glycerin and potassium bicarbonate. The active ingredient can also be dispersed in dentifrices, including: gels, pastes, powders and slurries. The active ingredient can be added in a therapeutically effective amount to a paste dentifrice that can include water, binders, abrasives, flavoring agents, foaming agents, and humectants.

The composition can be formulated in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formation, solutions will be administered in a manner compatible with the dosage formulation and in such a manner as it therapeutically effective. The formulations are easily administered in a variety of dosage forms such as injectable solutions, drug release capsules and the like.

In other embodiments, one may desire a topical application of compositions disclosed herein. Such compositions can be formulated in creams, lotions, solutions, or in solid form depending upon the particular application. The formulation of pharmaceutically acceptable vehicles for topical administration is well known to one of skill in the art (see, i.e., "Remington's Pharmaceuticals Sciences", 15.sup. Edition). Variation of the dosage of the compositions disclosed herein, will necessarily depend upon the particular subject, and the nature of the condition(s) being treated.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermic or intravenous fluid or injected at the proposed site of infusion, (see, for example, "Remington's Pharmaceutical Sciences", 15.sup. Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

EXAMPLE (1) Fractionation of Serenoa Repens Berries

In order to establish optimal conditions for preparing an extract from *Serenoa repens* (Saw Palmetto) berries, Super Critical Fluid (SCF) fractionation was carried out on the apparatus, shown as FIG. 2. This apparatus comprises a dual pump system, utilizing one syringe pump for neat supercritical near-critical or critical fluid and a second syringe pump for an alcohol co-solvent or modifier. The pumps are independently controllable, allowing easy adjustment of fluid composition.

To prepare a sample, the *Serenoa repens* biomass was ground into a fine powder (around 100 mesh). Three grams of the dried powder was transferred to a 10 mL extraction cartridge, after which the cartridge was filled with glass wool or beads to reduce the dead volume. After loading a cartridge on its holder, a sequential extraction/fractionation procedure was commenced. The system was then brought to 3,000 psig and 40° C., and extracted for 30 minutes with pure carbon dioxide ($CO_2$). This fraction was collected in either ethanol or methanol in the glass collection vessel, shown in FIG. 2. Next, the extraction parameters were typically set to: supercritical $CO_2$ at 3,000 psig and extraction temperature 40° C., step extractions with methanol or ethanol as a co-solvent at 5, 10, 20, 30 and 40 vol %, each step being 30 min. For SCF extraction and chromatographic purification (CXP) procedures, an inline HPLC column was introduced between the extractor and the backpressure regulator (FIG. 2) during the extraction step.

Several different experiments were conducted to establish optimal conditions for the SCF fractionation of *Serenoa repens* biomass and the resulting Saw Palmetto products. For example, *Serenoa repens* [Lot # 335H635115] from Wilcox Natural Products, Boone, N.C., was dried and ground to a fine powder. Three grams of *Serenoa repens* powder was fractionated using carbon dioxide and methanol at 3,000 psig and 40° C. The SCF extraction and fractionation (CXF) was carried out initially with neat carbon dioxide and then by incrementally adding methanol to increase the polarity of the working solvent in the apparatus (FIG. 2). The fractions were dried under vacuum at approximately 40° C. for 18 hours. The results of a typical CXF experiment are shown in Table 1.

TABLE 1

Fractionation of *Serenoa repens* Biomass (Wilcox) with SCF Carbon Dioxide/Methanol at 3,000 psig and 40° C. [SSP-1]

| Fraction | Description | Amt. Ext. (mg) | % Extracted |
|---|---|---|---|
| SSP-1A | Carbon Dioxide with 0% Methanol | 173.8 | 5.8 |
| SSP-1B | Carbon Dioxide with 5% Methanol | 15.2 | 0.5 |
| SSP-1C | Carbon Dioxide with 10% Methanol | 6.6 | 0.2 |
| SSP-1D | Carbon Dioxide with 20% Methanol | 6.6 | 0.2 |
| SSP-1E | Carbon Dioxide with 30% Methanol | 6.2 | 0.2 |
| SSP-1F | Carbon Dioxide with 40% Methanol | 4.1 | 0.1 |
| Total | | 212.5 | 7.0 |

The experiment conducted above was repeated with *Serenoa repens* obtained from R. J. Reynolds, Merry Hill, N.C. The results of the second fractionation experiment with carbon dioxide and methanol at 3,000 psig and 40° C. are shown in Table 2 below:

TABLE 2

Fractionation of *Serenoa repens* Biomass (RJR) with SCF Carbon Dioxide/Methanol at 3,000 psig and 40° C. [SSP-2]

| Fraction | Description | Amt. Ext. (mg) | % Extracted |
|---|---|---|---|
| SSP-2A | Carbon Dioxide with 0% Methanol | 32.0 | 1.1 |
| SSP-2B | Carbon Dioxide with 5% Methanol | 25.7 | 0.9 |
| SSP-2C | Carbon Dioxide with 10% Methanol | 19.5 | 0.7 |
| SSP-2D | Carbon Dioxide with 20% Methanol | 36.3 | 1.2 |
| SSP-2E | Carbon Dioxide with 30% Methanol | 46.3 | 1.5 |
| SSP-2F | Carbon Dioxide with 40% Methanol | 49.0 | 1.6 |
| Total | | 208.8 | 7.0 |

While the percent biomass extracted in total was approximately the same for these two experiments, conducted under similar conditions by the same operator, the distribution of the amount extracted as a function of polarity are quite different. Such differences could be due to differences in the composition of raw materials utilized. The developed manufacturing process must thus take into account the quality and consistency of the biomass raw materials. Subsequent experiments were all conducted with the same batch of *Serenoa repens* berries from Wilcox Natural Products. This batch was stored at −20° C. between sample withdrawals.

In all, seventeen (17) laboratory-scale SCF fractionation experiments, generating 84 data points, were conducted under different conditions of temperature, pressure and co-solvent concentration as well as biomass type and component, e.g. husks vs. kernels vs. berries. The results of these experiments are summarized in Table 3.

TABLE 3

Fractionation of *Serenoa repens* Biomass with SCF Carbon Dioxide/Methanol at Different Temperature & Pressures

| Experiment | Raw Material | SCF | Temp. (° C.) | Pressure (psig) | Extraction (%) |
|---|---|---|---|---|---|
| SSP-1 | Wilcox | $CO_2$/methanol | 40 | 3,000 | 14.95 |
| SSP-2 | RJReynolds | $CO_2$/methanol | 40 | 3,000 | 6.96 |
| SSP-3 | Wilcox | $CO_2$/methanol | Ambient | 3,000 | 14.50 |
| SSP-4 | Wilcox | $CO_2$/methanol | Ambient | 1,000 | 17.50 |

TABLE 3-continued

Fractionation of *Serenoa repens* Biomass with SCF
Carbon Dioxide/Methanol at Different Temperature & Pressures

| Experiment | Raw Material | SCF | Temp. (° C.) | Pressure (psig) | Extraction (%) |
|---|---|---|---|---|---|
| SSP-5 | Wilcox (kernels) | $CO_2$/methanol | 22 | 1,000 | 15.48 |
| SSP-6 | Wilcox (husks) | $CO_2$/methanol | 22 | 1,000 | 21.02 |
| SSP-7 | Wilcox | $CO_2$/methanol | 40 | 1,000 | 18.11 |
| SSP-8 | Wilcox | $CO_2$/methanol | 30 | 1,000 | 18.35 |
| SSP-9 | Wilcox | $CO_2$/methanol | 25 | 3,000 | 17.63 |
| SSP-10 | Wilcox | $CO_2$/methanol | 30 | 3,000 | 12.60 |
| SSP-11 | Wilcox | $CO_2$/methanol | 40 | 3,000 | 7.60 |
| SSP-12 | Wilcox | $CO_2$/methanol | 40 | 2,000 | 18.91 |
| SSP-13 | Wilcox | $CO_2$/methanol | 25 | 2,000 | 13.34 |
| SSP-14 | Wilcox | $CO_2$/methanol | 30 | 2,000 | 20.29 |
| *SSP-15* | *Wilcox* | $CO_{2/methanol}$ | *22* | *1,000* | *15.20* |
| *SSP-16* | *Wilcox (kernels)* | $CO_{2/methanol}$ | *22* | *1,000* | *15.99* |
| *SSP-17* | *Wilcox (husks)* | $CO_{2/methanol}$ | *22* | *1,000* | *20.32* |
| SSP-21 | Wilcox | Hexane | 25 | 0 | 12.0 |

All 84 fractions of the experiments listed in Table 3 were examined by thin layer chromatography (TLC) for phytosterols content. Normal-phase TLC methods were used for rapid, qualitative analysis of phytosterols. The stationary phase used was silica gel 60 $F_{254}$ precoated 9×18 cm TLC plates (250 μM) (EM Science). The mobile phase comprised hexane:ethyl acetate 65:35 with trace quantities of acetic acid. Campesterol, stigmasterol, β-sitosterol and stigmastanol standards were obtained from Sigma-Aldrich, St. Louis, Mo. Five μL volumes of both SSP fractions and reference solutions were each applied as an ~10 mm band. UV detection was made at 254 and 366 nm. The TLC plates were then dipped in a 5% ethanolic sulfuric acid, followed by 1% ethanolic vanillin. After heating at 110° C. for 5 min under observation, the plate was evaluated in visible light.

TLC indicated that SSP-4, SSP-5 and SSP-6 9 (italicized in Table 3) had the highest phytosterols content with the phytosterols primarily concentrated in the A (100% $CO_2$) and B (90% $CO_2$::5% methanol) fractions. These experiments were both conducted with SCF carbon dioxide at 1,000 psig and 22° C. with an ethanol co-solvent. Experiments SSP4, SSP-5 and SSP-6 were repeated respectively as SSP-15, SSP-16 and SSP-17 (also, italicized in Table 3). The average yields of SSP-15, SSP-16 and SSP-17 and SSP4, SSP-5 and SSP-6 were within 5% of each other. Such reproducibility is excellent and bodes well for process scale-up. These yields were also 50% higher that obtained by the traditional hexane extraction method (SSP-21 in Table 3). Based on phytosterol content by TLC, the optimal SCF conditions for producing an active Saw Palmetto extract were carbon dioxide at a temperature of 22° C. and a pressure of 1,000 psig. These conditions were not optimum for overall extraction yield as shown in Table 3 above.

Figure 3:
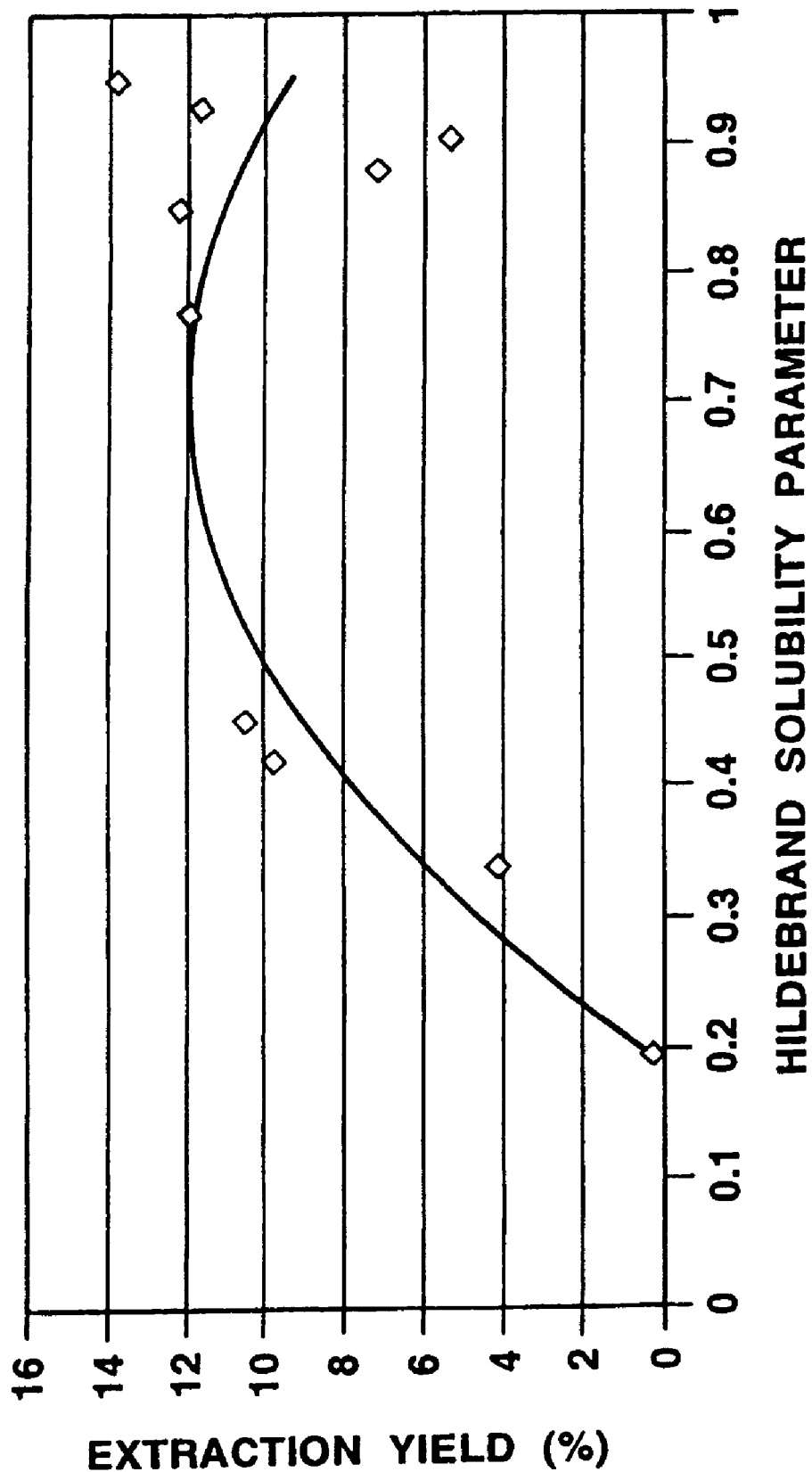
FIG. 3 is a graph of a Saw Palmetto extraction yield vs. Hildebrand solubility parameter of carbon dioxide.

The SCF Saw Palmetto yields are plotted as function of Hildebrand solubility parameter for SCF carbon dioxide/methanol in FIG. 3.

(2) In Virto Biological Activity of Saw Palmetoo SCF Fractions

An in vitro biological screen, inhibition of testosterone metabolism to dihydrotestosterone by 5-α reductase, was utilized to characterize and identify SCF CXP fractions that would be effective for benign prostatic hyperplasia (BPH). An excess of the enzyme, 5-α reductase, is directly linked to the etiology of benign prostatic hyperplasia. As such, the inhibition of this enzyme should result in the reduction in enlargement of the prostate gland.

The anti-androgenic activity of finasteride (a type II 5-α reductase inhibitor) has been the most common model for exploring the mode of action of Saw Palmetto. Literature review indicates that Saw Palmetto extract acts as a non-competitive, non-specific inhibitor of multiple testosterone metabolizing enzymes, including both type I and type II 5-α reductase (Delos et al., 1994), 17-β-hydoxysteroid dehydrogenases (Delos et al., 1995), and 3-ketosteroid reductase (Sultan et al., 1984). 5-α reductase and other membrane-bound enzymes are sensitive to perturbation of the lipid environment (Ichihara et al., 1989). Saw palmetto has equal potency in the inhibition of 5-α reductase type I and II. Neither inhibition is competitive like finasteride (Iehle et al., 1995). Saw palmetto may produce its inhibitory properties by modulating the lipid membrane-bound testosterone-metabolizing enzymes (Iehle et al., 1995). Saw palmetto inhibits testosterone metabolism, in vitro, in a variety of tissues from both rat and human (Sultan et al., 1984 and Delos et al., 1994).

The 5-α reductase inhibition assay, designed to evaluate inhibition of testosterone metabolism, is a two-step assay: the enzymatic reaction itself and the HPLC quantitation of the disappearance of one of the substrates (testosterone in our case) of the enzyme. First, saw palmetto fractions are incubated with a 5-α reductase preparation in the presence of androgen. After a specified incubation time, the remaining androgen is extracted and quantified by HPLC. The bioassay was first optimized with regards to: enzyme concentration and activity; amount of substrates (cofactor, androgen used); and reaction time. Ethanol was used as the diluent or extraction solvent since it either completely dissolves or gives uniform and stable slurries of Saw Palmetto products. Progesterone was used as an internal standard (ISTD) for HPLC since it is detectable at the same wavelength with similar sensitivity to testosterone and good baseline separations. All samples were run in triplicate.

The 5-α reductase inhibition assay was conducted by Paracelsian, Inc., Ithaca, N.Y. The recovery of ISTD was >96%; limits of detection (LOD) and limits of quantification (LOQ) were 50 and 200 nanograms (ng) respectively. The dose responses were linear and the working concentrations were determined to be 10 μg. The recovery of testosterone was independent of the amount present in the tested 1 to 11

μM; LOD and LOQ were 30 and 130 ng respectively. The working concentration was around 6.5 μg. All samples were run in triplicate.

Fifty micrograms of factions A, B and C of SSP-15, SSP-16 and SSP-17 were evaluated for in vitro biological activity in a 5-α reductase assay. The results of these assays are summarized in Table 4.

TABLE 4

Inhibition of 5-α-Reductase by SCF Saw Palmetto Fractions [Carbon Dioxide/Methanol at 1,000 psig and 22° C.]

| Fraction | % Inhibition | Average (%) | S.D. |
|---|---|---|---|
| *Serenoa repens* Berries | | | |
| Reference | 56, 55, 53 | 54.7 | 1.5 |
| SSP-15A | 54, 54, 55 | 54.3 | 0.6 |
| SSP-15B | 49, 51, 52 | 50.7 | 1.5 |
| SSP-15C | 9, 8, 8 | 8.3 | 0.6 |
| *Serenoa repens* Kernels | | | |
| Reference | 56, 55, 53 | 54.6 | 1.5 |
| SSP-16A | 34, 34, 32 | 33.3 | 1.2 |
| SSP-16B | 4, 3, 2 | 3.0 | 1.0 |
| SSP-16C | 7, −1, 2 | 2.7 | 4.0 |
| *Serenoa repens* Husks | | | |
| Reference | 53, 55 | 54.0 | 1.0 |
| SSP-17A | 55, 55, 55 | 55.0 | 0.0 |
| SSP-17B | 53, 58, 54 | 55.0 | 2.6 |
| SSP-17C | 34, 37, 37 | 36.0 | 1.7 |

Certificates of Analysis for SSP-15, SSP-16 and SSP-17 are shown as FIGS. 4 and 5. SSP-15A, SSP-17A and SSP-17B fractions are just as bioactive against 5-α reductase as the reference standard, Premixon, manufactured by Pierre Fabre, France. These fractions were also as bioactive as the Sabalselect™ product manufactured by Indena, Italy. As such, one optimal SCF condition appears to be near-critical $CO_2$ at 1,000 psig and 22° C.—an optimal condition for isolating phytosterols from Saw Palmetto berries. An optimal fraction appears to be the A fraction because it has the highest yield, e.g., 10.5 wt. % of the *Serenoa repens* fruit on a dry weight basis in SSP-15A The SCF fractionation experiments were not exhaustive in that each fraction was taken at a fixed time of 30 minutes. With longer extractions, the additional 2.5 wt. % extracted in SSP-15B will be removed in the first extraction step (SSP-15A).

The data in Table 4 suggests that the husks are more biologically active than the kernels of *Serenoa repens*. However, for fraction A, the whole berry appears to be just as biologically active as the kernels. Consequently, the husking of the berries may not significantly benefit the manufacturing process.

(3) Extraction of *Serenoa Repens* Scale-Up

The SCF fractionation process was scaled up by a factor of 16, and experimental runs were conducted with neat carbon dioxide using the conditions of 1,000 psig and 22° C. in a scaled-up version of the apparatus as shown in FIG. 2. The extraction volume was 88 mL (25.3 cm long with an ID of 2.1 cm) and packed with 48.3 g of ground *Sereona repens* (Wilcox Farm). The experimental design run sheet for SSP-18 is shown in Table 5.

TABLE 5

Experimental Run Sheet for Scale-Up of SCF Extraction of *Serenoa Repens* [Carbon Dioxide at 1,000 psig and 22° C.-SSP-18]

| Fraction | Flow Rate (mL/min) | System Volumes | Volume (mL) | Process Time (min) |
|---|---|---|---|---|
| A1 | 10.0 | 7.2 | 631 | 63 |
| A2 | 10.0 | 7.2 | 631 | 63 |
| A3 | 10.0 | 7.2 | 631 | 63 |
| A4 | 10.0 | 7.2 | 631 | 63 |
| Total | | 28.8 | 2,524 | 252 |

The results of the scaled-up SSP-18 SCF extraction of *Serenoa repens* berries are summarized in Table 6.

TABLE 6

Experimental Results from Scale-Up of SCF Extraction of *Serenoa Repens* [Carbon Dioxide at 1,000 psig and 22° C.-SSP-18]

| Expt. No. | SCF | Pressure (psig) | Temp. (C.) | Chrom. Column | Methanol (vol %) | Fraction | Weight (mg) | Extract (wt %) |
|---|---|---|---|---|---|---|---|---|
| SPP-18 | CO2 | 1,000 | 22 | None | 0.0 | A1 | 5,668.60 | 11.74 |
| | | | | | 0.0 | A2 | 334.90 | 0.69 |
| | | | | | 0.0 | A3 | 66.50 | 0.14 |
| | | | | | 0.0 | A4 | 42.20 | 0.09 |
| | | | | | | Total | 6,112.20 | 12.65 |

In SSP-18, 12.65 wt. % of the biomass was extracted; this compares well with the 12.91 wt. % extracted in fractions SSP-15A and SSP-15B, both of which were very bioactive. About 93% of the 12.65 wt. % yield in SSP-18 was recovered in the first 63 minute segment of this experimental run. This data was positive in two ways: (1) a co-solvent will not be required in a commercial-scale process; and (2)>90% yield can be obtained within the first hour of processing. Both these items significantly impact manufacturing economics, especially the latter that will increase materials throughput per unit size of capital equipment.

(4) SCF Extraction & Chromatographic Purification (CXP) of *Serenoa Repens*

SCF extraction and chromatographic purification (CXP) experiments were conducted on a scaled-up version of the apparatus shown as FIG. 2 with either an inline $C_{18}$ or an inline silica column having a volume of 10 mL (12.7 cm×ID=1.02 cm). The $C_{18}$ had a particle size of 40 μm and a pore size of 100 Å [Millipore, Batch # 3863-120A]; the silica had a particle size range of 0.063 to 0.200 mm [EM Science]. These experiments were each conducted with 48.3 grams of ground *Serenoa repens* whole fruit. Experimental yields are summarized in Table 7; and bioactivities are shown in Table 8. Certificate of analyses are shown in FIG. 6 and the raw data is presented in Table 9.

TABLE 7

Experimental Yields from Scale-Up SCF Extraction and Chromatographic Purification (CXP) of *Serenoa Repens*
[Carbon Dioxide at 1,000 psig and 22° C.-SSP-19 and SSP-20]

| Expt. No. | SCF | Pressure (psig) | Temp. (C.) | Chrom. Column | Methanol (vol %) | Fraction | Weight (mg) | Extract (wt %) |
|---|---|---|---|---|---|---|---|---|
| SPP-19 | CO2 | 1,000 | 22 | C18 | 0.0 | A | 5578.90 | 11.55 |
|  |  |  |  |  | 100.0 | CF | 441.30 | 0.91 |
| Total |  |  |  |  |  |  | 6020.20 | 12.46 |
| SSP-20 | CO2 | 1,000 | 22 | Silica | 0.0 | A | 3593.00 | 7.44 |
|  |  |  |  |  | 100.0 | CF | 1868.50 | 3.87 |
| Total |  |  |  |  |  |  | 5461.50 | 11.31 |

TABLE 8

Inhibition of 5-α-Reductase by SCF Saw Palmetto Fractions Produced by SCF Extraction and Chromatographic Purification (CXP) of *Serenoa Repens* [Carbon Dioxide at 1,000 psig and 22° C.-SSP-19 and SSP-20]

| Fraction | % Inhibition | Average (%) | S.D. |
|---|---|---|---|
| $C_{18}$ Chromatographic Column | | | |
| Reference | 57, 60, 58 | 58.3 | 1.5 |
| SSP-19-A | 63, 63, 60 | 62.0 | 1.7 |
| SSP-19-CF | 4, 3 | 3.5 | 1.0 |
| Silica Chromatographic Column | | | |
| Reference | 57, 60, 58 | 58.3 | 1.5 |
| SSP-20-A | 54, 53, 54 | 53.7 | 0.6 |
| SSP-20-CF | 54, 48, 47 | 49.7 | 3.8 |

TABLE 9

Raw Data for 5-α Reductase Inhibition of SCF Saw Palmetto Fractions
[SSP-19AF and SSP-20AF]
5-α REDUCTASE RAW DATA AND RESULTS NB: 1101-184  Date: Mar. 20, 2001  Client: Aphios

| | Uncorrected Area | | | | Corrected Area | | | |
|---|---|---|---|---|---|---|---|---|
| | TE (Peak Area) | PE (Peak Area) | STD PE Average Peak Area | PE Recovery Fraction | TE (Individual) | TE (Average) | TE (no Inhibition) | TE (Sample Inhibition) |
| Assay Code | A | B | C | D | E | F | G | H |
| (−) 1 | 512.4 | 351.3 |  | 1.00 | 513.0 | 513.2 |  |  |
| (−) 2 | 478.0 | 328.2 |  | 0.93 | 512.2 |  |  |  |
| (−) 3 | 516.5 | 353.2 |  | 1.00 | 514.3 |  |  |  |
| (+) 1 | 190.3 | 344.0 |  | 0.98 | 194.6 | 197.0 | 316.12 |  |
| (+) 2 | 196.0 | 356.5 |  | 1.01 | 193.4 |  |  |  |
| (+) 3 | 200.8 | 347.5 |  | 0.99 | 203.2 |  |  |  |
| R 1 | 348.1 | 325.6 |  | 0.93 | 376.0 |  |  | 179.0 |
| R 2 | 395.3 | 358.7 |  | 1.02 | 387.6 |  |  | 190.5 |
| R 3 | 402.6 | 372.9 |  | 1.06 | 379.7 |  |  | 182.7 |
| A 1 | 381.7 | 339.8 |  | 0.97 | 395.1 |  |  | 198.0 |
| A 2 | 417.9 | 370.4 |  | 1.05 | 396.8 |  |  | 199.8 |
| A 3 | 381.3 | 347.3 |  | 0.99 | 386.1 |  |  | 189.1 |
| B 1 | 211.8 | 355.1 |  | 1.01 | 209.8 |  |  | 12.7 |
| B 2 |  |  |  |  |  |  |  |  |
| B 3 | 216.3 | 366.8 |  | 1.04 | 207.4 |  |  | 10.3 |
| C 1 | 317.5 | 304.4 |  | 0.87 | 366.8 |  |  | 169.8 |
| C 2 | 296.9 | 287.1 |  | 0.82 | 363.7 |  |  | 166.7 |
| C 3 | 371.5 | 355.2 |  | 1.01 | 367.8 |  |  | 170.8 |
| D 1 | 396.2 | 380.4 |  | 1.08 | 366.3 |  |  | 169.3 |
| D 2 | 312.7 | 315.4 |  | 0.90 | 348.7 |  |  | 151.6 |
| D 3 | 375.9 | 381.1 |  | 1.08 | 346.9 |  |  | 149.9 |
| STD 1 | 493.1 | 357.6 | 351.7 |  |  |  |  |  |
| STD 2 | 484.6 | 349.7 |  |  |  |  |  |  |
| STD 3 | 477.0 | 347.8 |  |  |  |  |  |  |

TABLE 9-continued

Raw Data for 5-α Reductase Inhibition of SCF Saw Palmetto Fractions
[SSP-19AF and SSP-20AF]
5-α REDUCTASE RAW DATA AND RESULTS

| | Client: Aphios | | | | Analyst: Barry Hughes | | | |
|---|---|---|---|---|---|---|---|---|
| | Statistical Analysis | | | | Sample ID | | Results | |
| | Individual % Inhibition | Average % Inhibition | Standard Deviation | Coefficient of Variation (CV) | Client Sample Code | Paracelsian Herb Locker Code | Assay Compliance | Sample (Pass/Fail) |
| | | | | Column | | | | |
| Assay Code | I | J | K | L | M | N | O | P |
| (−) 1 | | | | | | | | |
| (−) 2 | | | | | | | | |
| (−) 3 | | | | | | | | |
| (+) 1 | | | | | | | | |
| (+) 2 | | | | | | | | |
| (+) 3 | | | | | | | | |
| R 1 | 57% | 58.0 | 1.9 | 3.0 | Permixon | 05-022 | YES | PASS |
| R 2 | 60% | | | | 50 μg | | | |
| R 3 | 58% | | | | | | | |
| A 1 | 63% | 62.0 | 1.8 | 3.0 | Aphios SSP | 05-084 | YES | PASS |
| A 2 | 63% | | | | 19-1 50 μg | | | |
| A 3 | 60% | | | | | | | |
| B 1 | 4% | 4.0 | 0.5 | 15.0 | Aphios SSP | 05-085 | YES | FAIL |
| B 2 | | | | | 19-cf 50 μg | | | |
| B 3 | 3% | | | | | | | |
| C 1 | 54% | 53.0 | 0.7 | 1.0 | Aphios SSP | 05-086 | YES | PASS |
| C 2 | 53% | | | | 20-1 50 μg | | | |
| C 3 | 54% | | | | | | | |
| D 1 | 54% | 50.0 | 3.4 | 7.0 | Aphios SSP | 05-087 | YES | PASS |
| D 2 | 48% | | | | 20-cf 50 μg | | | |
| D 3 | 47% | | | | | | | |
| STD 1 | | | | | | | | |
| STD 2 | | | | | | | | |
| STD 3 | | | | | | | | |

LEGEND
SAMPLE AND EXPERIMENTAL CODE
TE = Testosterone = Androgen = TEST STEROID
PE = Progesterone = INTERNAL STNDARD (ISTD)
(−) = NO NADPH = 100% 5-α Reductase Inhibition
(+) = PLUS NADP = NO 5-α Reductase Inhibition
R 1, R 2, R 3 = Reference material (PERMIXON)
A 1, A 2, A 3, . . . , F 1, F 2, F 3 = TEST SAMPLES
STD 1, STD 2, STD 3 = (PE + TE) Direct HPLC, NO Incubation
SAMPLE PASS/FAIL CRITERIA
O = Assay compliance = YES for CV < 20%; = NO for CV ≧
P = Sample ≧ Lower 99% Confidence Limit = PASS
P = Sample < Lower 99% Confidence Limit = FAIL
Lower confidence Limit = 45% Inhibition
COLUMN CODE
D = B/C = Recovery fraction of IST
E = A/D = Corrected TE area
G = F(−) − F(+) = TE (No Inhibition)
H = E − F(+) = TE (Sample Inhibition
I = H/G(+) = Sample % Inhibition
J = I (Average)
K = I (Standard Deviation)
L = I (Coefficient of Variation The biological activity of SSP-19-A is about 15% greater than SSP-15A (see Table 4) that was extracted at the same conditions and produced an average 5-α reductase inhibition of 54.3%. SSP-19-A was the product recovered after the extracting stream had flowed through from the $C_8$ column in a single fraction. SSP-19-A, manufactured in a single step SCF CXP (extraction and chromatography) process is superior to Permixon and Sabalselect™, SSP-19-CF, the $C_{18}$ column flush, had little biological activity.

The silica column in SSP-20 was inefficient in enhancing the bioactivity of the SCF Saw Palmetto fraction, even though the bioactivity of the flow-through fraction was similar to the standard. The scaled-up experiments (SSP-18 through SSP-20) thus produced fractions that were as active, and in one specific and novel case, more active than the reference standard.

(5) Chemical Characterization of SCF Saw Palmetto Fractions

The phytosterol content and fatty acid chemistry of the bioactive fractions were measured by thin layer chromatography (TLC) and gas chromatography (GC).

Figure 7:
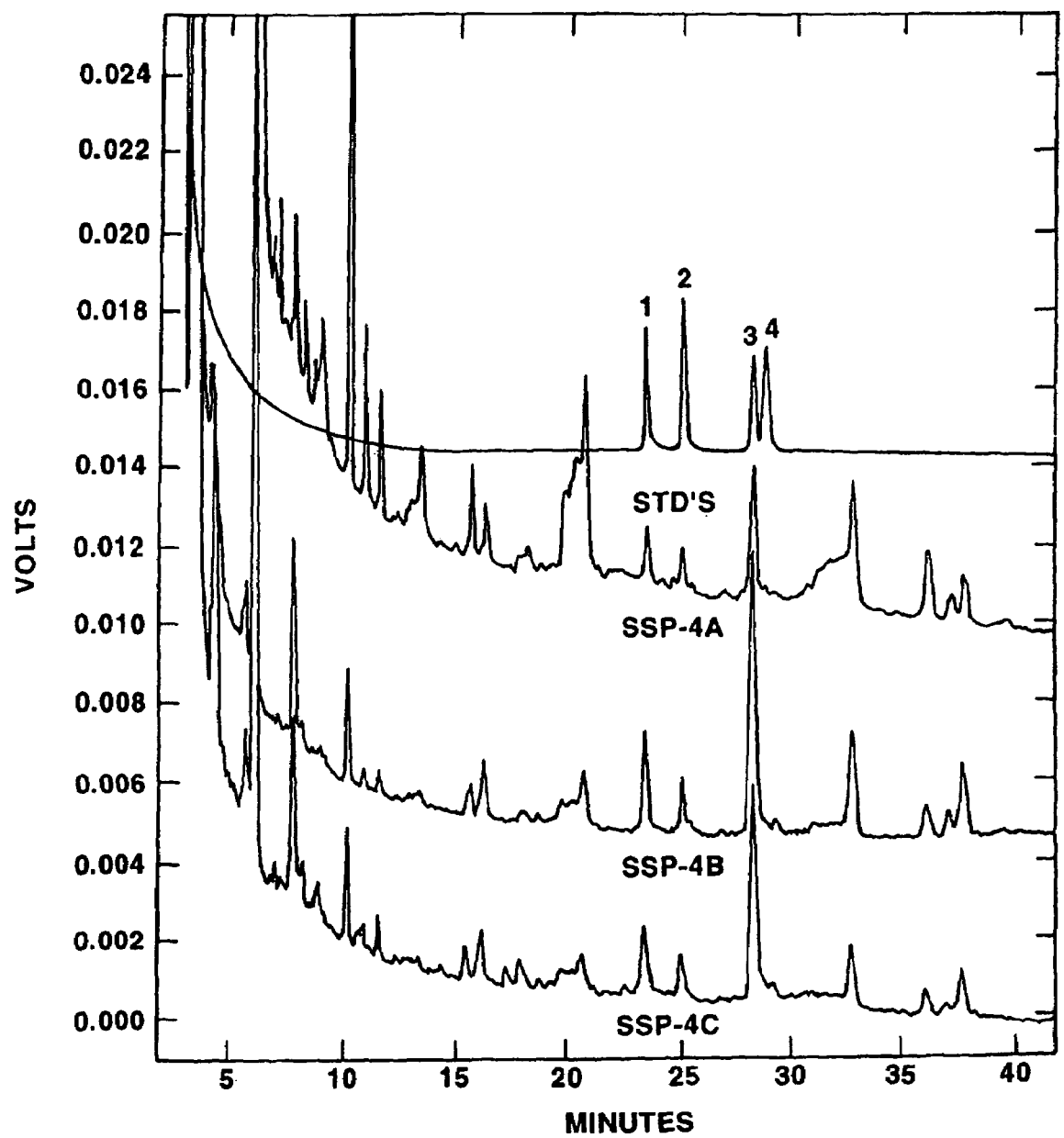
FIG. 7 is a compilation of gas chromatograms of Saw Palmetto fractions SSP-4A, B & C.
Figure 8:
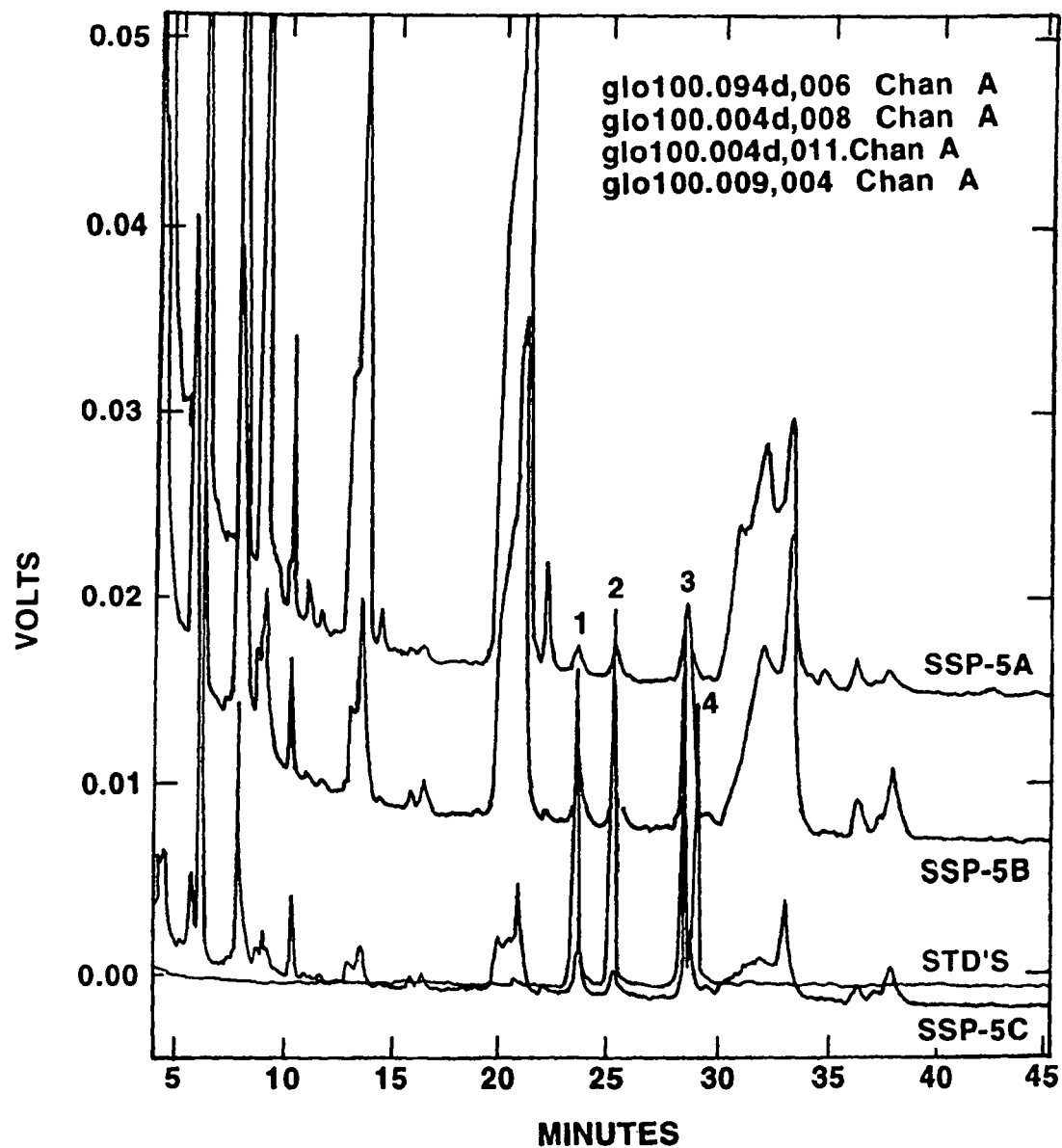
FIG. 8 is a compilation of gas chromatograms of Saw Palmetto fractions SSP-5A, B & C.
Figure 9:
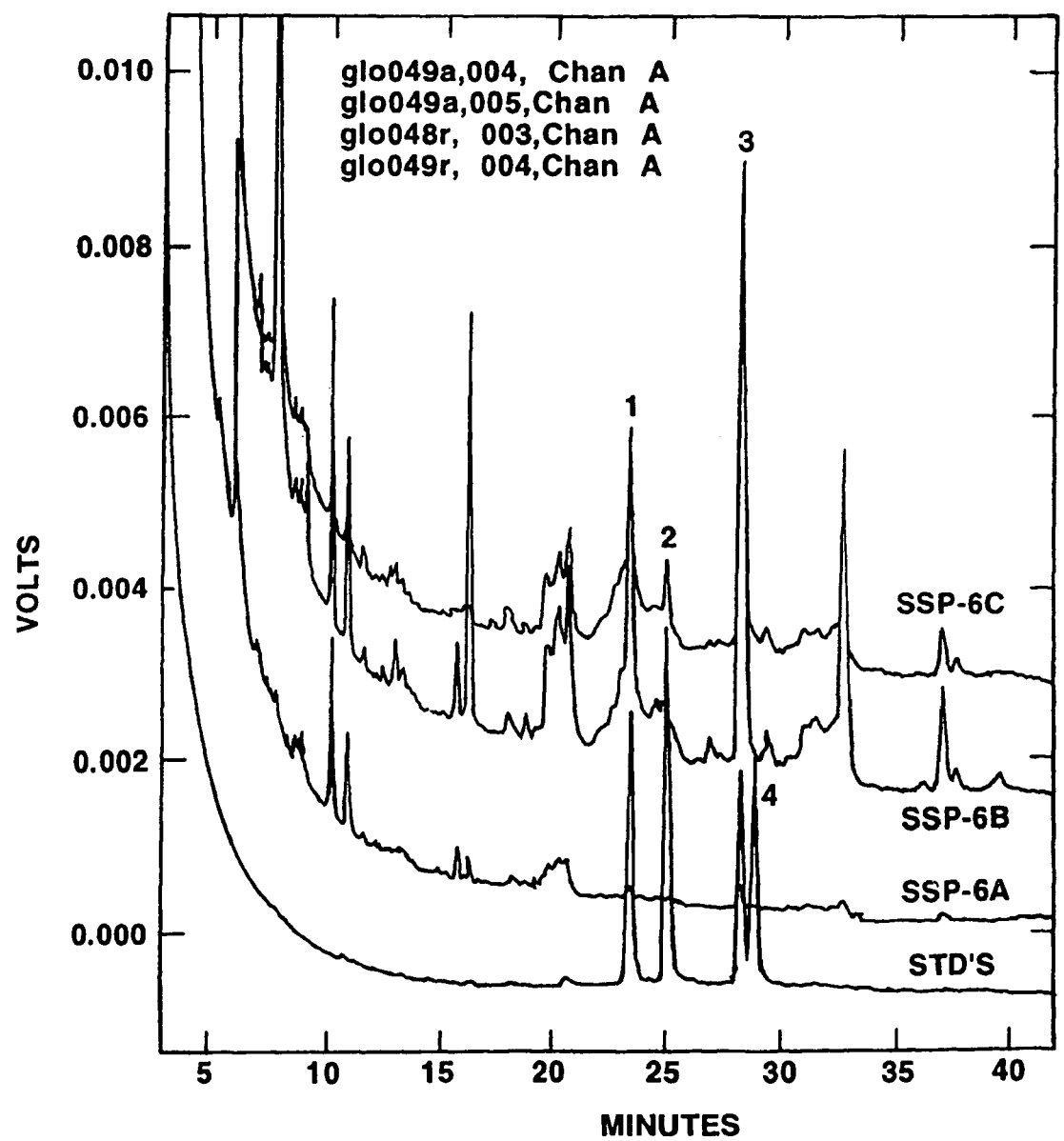
FIG. 9 is a compilation of gas chromatograms of Saw Palmetto fractions SSP-6A, B & C.

The phytosterol content of SSP4, SSP-5 and SSP-6 were measured by gas chromatography (GC) by Green Laboratories, Windham, Me. The samples were weighed in replicate and dissolved in chloroform by sonication or vortex mixing. Standards of campesterol, stigmasterol, β-sitosterol and stigmastanol were extracted in a similar manner. Two μL of the samples and standards were injected at a 1:10 split ratio into a Shimadzu GC-17A gas chromatograph with a Supelco SAC-5 column (30 m, 0.25 mm ID, 0.15 μm film thickness). The data is summarized in Table 10; GC chromatograms of SSP-4, SSP-5 and SSP-6 are respectively shown in FIGS. 7, 8 and 9. From a mass extracted standpoint, the yield from the whole berry appears to be an average of the yields from the kernels and husks (data not shown). Similarly, on a phytosterols basis except for campesterol, the yield from the berry is an average of the yields from the kernels and husks.

TABLE 10

Phytosterol Content SCF Saw Palmetto Fractions
[Carbon Dioxide/Methanol at 1,000 psig and 22° C.]

| Fraction | $CO_2:CH_3OH$ | Campesterol (mg/gm) | Stigmasterol (mg/gm) | β-sitosterol (mg/gm) | Stigmastanol (mg/gm) | Total Phytosterols |
|---|---|---|---|---|---|---|
| *Serenoa repens* Berry or Fruit | | | | | | |
| SSP-4A | 100:0 | 0.17 | 0.28 | 0.68 | 0.14 | 1.27 |
| SSP-4B | 95:5 | 1.06 | 1.15 | 5.49 | 0.00 | 7.70 |
| SSP-4C | 90:10 | 0.64 | 0.69 | 3.69 | 0.00 | 5.02 |
| Total | | 1.87 | 2.12 | 9.86 | 0.14 | 13.99 |
| *Serenoa repens* Kernels | | | | | | |
| SSP-5A | 100:0 | 0.26 | 0.46 | 1.15 | 0.00 | 1.87 |
| SSP-5B | 95:5 | 1.27 | 1.83 | 6.08 | 0.00 | 9.18 |
| SSP-5C | 90:10 | 0.97 | 0.95 | 6.00 | 0.00 | 7.92 |
| Total | | 2.50 | 3.24 | 13.23 | 0.00 | 18.97 |
| *Serenoa repens* Husks | | | | | | |
| SSP-6A | 100:0 | 0.06 | 0.03 | 0.21 | 0.02 | 0.32 |
| SSP-6B | 95:5 | 1.47 | 0.63 | 3.19 | 0.00 | 5.29 |
| SSP-6C | 90:10 | 1.38 | 0.65 | 2.49 | 0.00 | 4.52 |
| Total | | 2.91 | 1.31 | 5.89 | 0.02 | 10.13 |

(6) Saw Palmetto and Sperol

The fractions, SSP-15A and SSP-17A, manufactured in a single step SCF CXP (extraction only) process was shown by an in vitro biological assay to be statistically equivalent to Permixon, the reference standard, manufactured by Pierre Fabre, France (see Table 4). A dose response curve of SSP-15A and Permixon is shown to almost identical in FIG. 10. A Certificate of Analysis for this data is shown as FIG. 11, and the raw data is itemized in Table 11.

Figure 12:
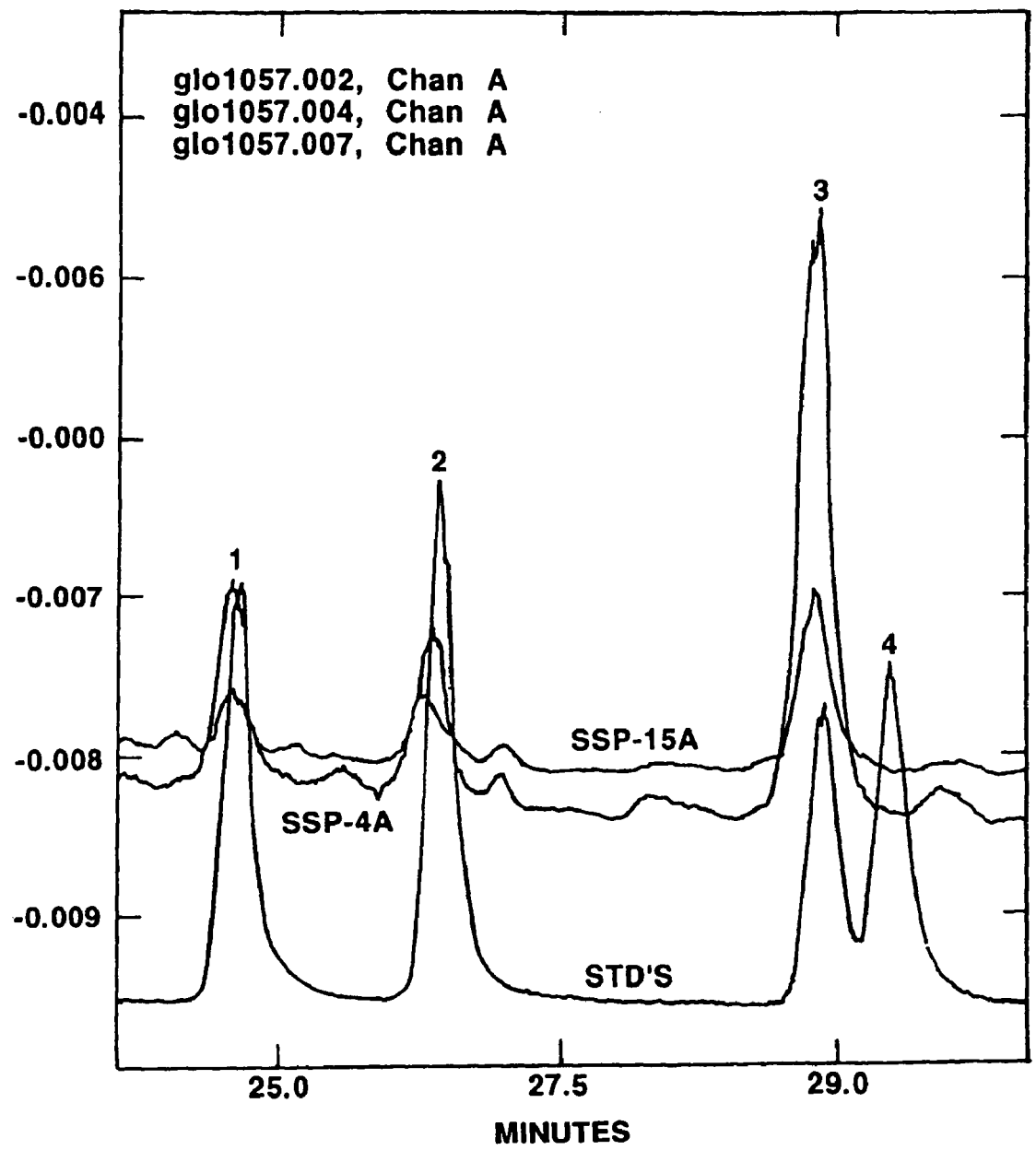
FIG. 12 is a compilation of gas chromatograms of Saw Palmetto fractions SSP-4A & 15-A.
Figure 13:
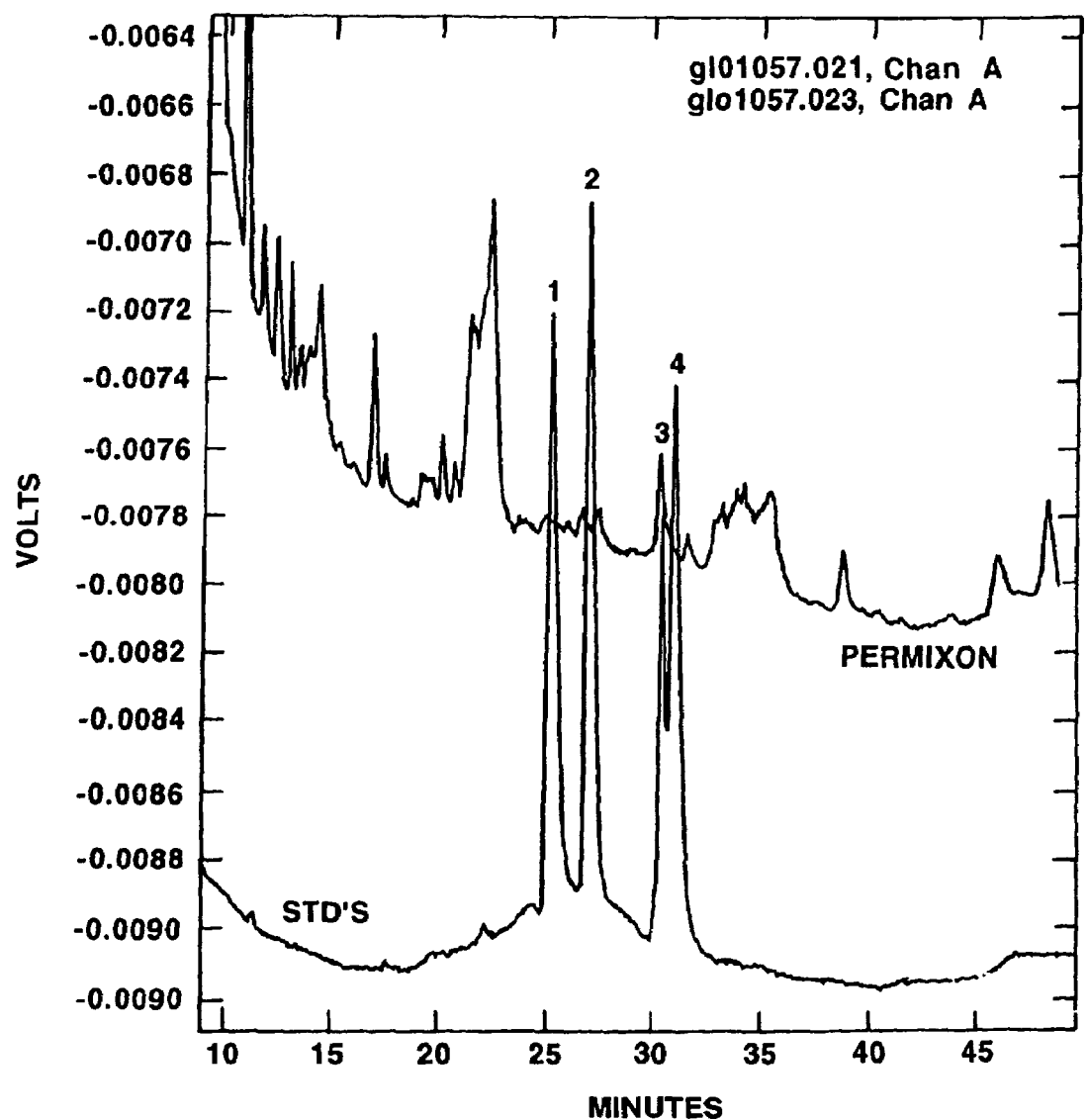
FIG. 13 is a gas chromatograms of Permixon.

The phytosterols chemistries of SSP-15A and Permixon were also compared by GC analyses (FIGS. 12 and 13). This comparison is shown in Table 12, which also contains published data on Indena's Sabalselect™ product that is manufactured supercritical $CO_2$ at 45° C. and 3,240 psig.

TABLE 12

Comparison of Phytosterol Content SCF Saw Palmetto and Permixon

| Fraction | Campesterol (mg/gm) | Stigmasterol (mg/gm) | β-sitosterol (mg/gm) | Stigmastanol (mg/gm) | Total Phytosterols |
|---|---|---|---|---|---|
| SSP-15A | 0.016 | 0.060 | 0.106 | 0.00 | 0.182 |
| Permixon | 0.003 | 0.015 | 0.055 | 0.00 | 0.073 |
| Sabalselect ™ | 0.07 | 0.03 | 0.22 | NR | 0.32 |

NR—not reported

Figure 10:
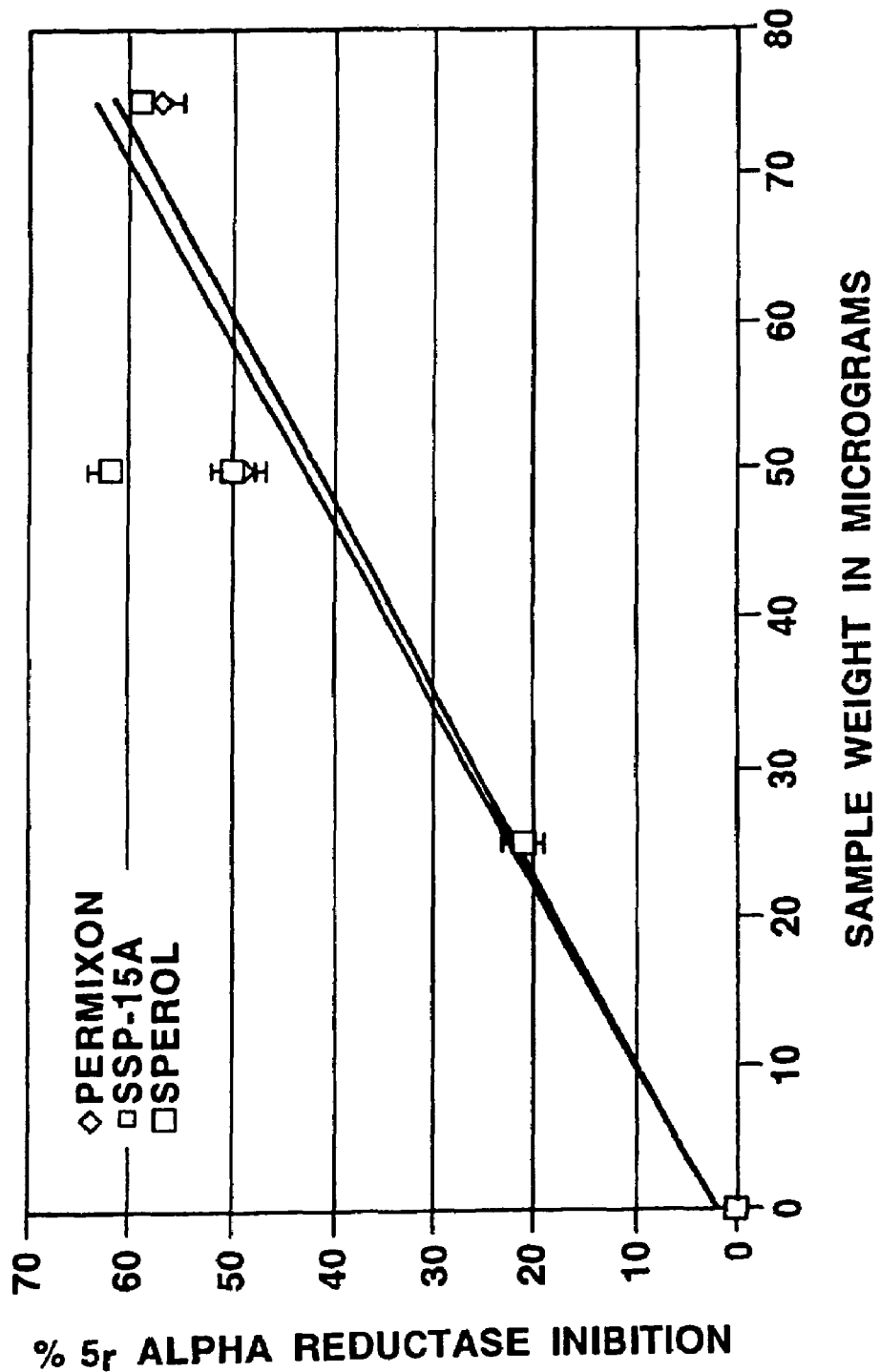
FIG. 10 is a dose response curve for Saw Palmetto and Permixon.

A SCF fraction such as SSP-15A can be utilized to manufacture an active Saw Palmetto product. A SCF fraction such as SSP-19-1 can be utilized to manufacture an active Sperol product. This Sperol product is of significance due to its enhanced bioactivity with regard to inhibiting the 5-α reductase enzyme as shown in FIG. 10.

TABLE 11

Raw Data for 5-α Reductase Inhibition of SCF Saw Palmetto Fractions
[SSP-15A-25 µg, 50 µg 75 µg]
5 α-Reductase Raw Data and Results Notebook Code: 1116-92  Date: Feb. 16, 2001  Client:  Analyst: Martha Jensen

| | | | uncorrected area | | | corrected area | | | | statistical analysis | | | results | |
|---|---|---|---|---|---|---|---|---|---|---|---|---|---|---|
| | berb locker code | sample identification | TE peak area | PE peak area | STD PE average peak area | PE recovery fraction | TE indiv. | TE ave. | TE no inhib. | TE sample inhib. | individual % inhibition | average % inhibition | standard deviation | coefficient of variation | assay compliance | extract pass/fail |
| n sample code | | | A | B | C | D | E | F | G | H | I | J | K | L | M | N |
| 1 (−)1 | | | 562.2 | 380.4 | | 1.02 | 553.5 | 572.4 | | | | | | | | |
| 2 (−)2 | | | 574.1 | 368.4 | | 0.98 | 583.5 | | | | | | | | | |
| 3 (−)3 | | | 553 | 356.5 | | 0.95 | 580.3 | | | | | | | | | |
| 4 (+)1 | | | 174.9 | 356.5 | | 0.95 | 183.7 | 178.5 | 393.9 | | | | | | | |
| 5 (+)2 | | | 162.3 | 375.9 | | 1 | 181.5 | | | | | | | | | |
| 6 (+)3 | | | 163.7 | 358.8 | | 0.96 | 170.2 | | | | | | | | | |
| 7 R1 | 05-022 | Permixon | 349.5 | 344.1 | | 0.92 | 380.3 | | | 201.8 | 51% | 51% | 1% | 2% | Yes | Pass |
| 8 R2 | | | 396.2 | 388.8 | | 1.04 | 381.6 | | | 203.1 | 52% | | | | | |
| 9 R3 | | | 341.9 | 343.5 | | 0.92 | 372.8 | | | 194.3 | 49% | | | | | |
| 10 A1 | 05-074 | SP-15-A 75 µg | 426.2 | 397.7 | | 1.06 | 401.3 | | | 222.8 | 57% | 57% | 2% | 3% | Yes | Pass |
| 11 A2 | | | 436.5 | 412.2 | | 1.1 | 396.6 | | | 218.1 | 55% | | | | | |
| 12 A3 | | | 418.9 | 383 | | 1.02 | 409.7 | | | 231.2 | 59% | | | | | |
| 13 B1 | 05-074 | SP-15-A 50 µg | 284.7 | 397 | | 1.06 | 363 | | | 184.5 | 47% | 49% | 2% | 4% | Yes | Pass |
| 14 B2 | | | 402.9 | 397.3 | | 1.06 | 379.8 | | | 201.3 | 51% | | | | | |
| 15 B3 | | | 383.2 | 386.1 | | 1.03 | 371.7 | | | 193.2 | 49% | | | | | |
| 16 C1 | 05-074 | SP-15-A 25 µg | 276.7 | 389.4 | | 1.04 | 266.2 | | | 87.7 | 22% | 21% | 1% | 7% | Yes | Fail |
| 17 C2 | | | 242.3 | 355.5 | | 0.95 | 255.2 | | | 76.7 | 19% | | | | | |
| 18 C3 | | | 278.4 | 398.7 | | 1.06 | 261.5 | | | 83.0 | 21% | | | | | |
| 19 D1 | 05-022 | Permixon 75 µg | 440.8 | 407.2 | | 1.09 | 405.4 | | | 227.0 | 58% | 59% | 1% | 2% | Yes | Pass |
| 20 D2 | | | 413.6 | 373.0 | | 1.00 | 415.3 | | | 236.8 | 60% | | | | | |
| 21 D3 | | | 455.9 | 415.3 | | 1.11 | 411.1 | | | 232.6 | 59% | | | | | |
| 22 E1 | 05-022 | Permixon 50 µg | 418.4 | 417.2 | | 1.11 | 375.5 | | | 197.0 | 50% | 49% | 2% | 3% | Yes | Pass |
| 23 E2 | | | 407.1 | 416.8 | | 1.11 | 365.8 | | | 187.3 | 48% | | | | | |
| 24 E3 | | | 398.2 | 395.1 | | 1.05 | 377.5 | | | 199.0 | 51% | | | | | |
| 25 F1 | 05-022 | Permixon 25 µg | 291.2 | 405.6 | | 1.08 | 268.9 | | | 90.4 | 23% | 21% | 2% | 7% | Yes | Fail |
| 26 F2 | | | 272.2 | 396.9 | | 1.06 | 256.8 | | | 78.3 | 20% | | | | | |
| 27 F3 | | | 184.4 | 263.8 | | 0.70 | 261.8 | | | 83.3 | 21% | | | | | |
| 28 STD1 | | | 523.8 | 377.2 | 374.5 | | | | | | | | | | | |
| 29 STD2 | | | 518.9 | 372.0 | | | | | | | | | | | | |
| 30 STD3 | | | 502.5 | 374.2 | | | | | | | | | | | | |

Column Code

LEGEND
SAMPLE AND EXPERIMENTAL CODE
TE = testosterone = androgen = test steroid
PE = progesterone = internal standard (ISTD)

TABLE 11-continued

Raw Data for 5-α Reductase Inhibition of SCF Saw Palmetto Fractions
[SSP-15A-25 µg, 50 µg 75 µg]
5 α-Reductase Raw Data and Results

| Notebook Code: 1116-92 | | | Date: Feb. 16, 2001 | | | | Client: | | | | Analyst: Martha Jensen | | | |
|---|---|---|---|---|---|---|---|---|---|---|---|---|---|---|
| | uncorrected area | | | | | corrected area | | | | | statistical analysis | | | results |
| berb locker code | sample identification | TE peak area | PE peak area | STD PE average peak area | PE recovery fraction | TE indiv. | TE ave. | TE no inhib. | TE sample inhib. | individual % inhibition | average % inhibition | standard deviation | coefficient of variation | assay compliance | extract pass/ fail |
| | | | | | | | Column Code | | | | | | | | |
| n sample code | | A | B | C | D | E | F | G | H | I | J | K | L | M | N |

(−) = no NADPH = 100% 5-a reductase inhibition
(+) = plus NADPH = NO 5-a Reductase inhibition
R 1, R 2, R 3 = reference material (Permixon)
A 1, A 2, A 3, . . . , F 1, F 2, F 3 = test samples
STD 1, STD 2, STD 3 = (PE + TE) direct HPLC
SAMPLE PASS/FAIL CRITERIA
M = CV < 20% = Yes CV ≥ 20% = No
N = Sample ≥ Lower 99% confidence limit = PASS
N = Sample < Lower 99% confidence limit = FAIL
Lower confidence limit = 45% inhibition
COLUMN CODE
D = B/C = recovery fraction of ISTD
E = A/D = corrected TE area
G = F(−) − F(+) = no inhibition
H = E − F(+) = sample inhibition
I = H/G(+) = sample % inhibition While this invention has been particularly shown and described with references to specific embodiments, it will be understood by those skilled in the art that various changes in form and details may be made therein without departing from the spirit and scope of the invention as defined by the appended claims.

What is claimed is:

1. A method of preparing a 5-α-reductase inhibitor preparation, comprising the following steps:

(a) grinding Saw Palmetto berries into a 100-mesh powder;
(b) extracting said powder with carbon dioxide at 1,000 psig and 22° C.;
(c) passing said carbon dioxide extract at 1,000 psig and 22° C. through an in-line C18 column; and
(d) collecting a 5-α reductase inhibitor preparation.

* * * * *